(12) United States Patent
Baarman

(10) Patent No.: US 9,036,371 B2
(45) Date of Patent: *May 19, 2015

(54) ADAPTIVE INDUCTIVE POWER SUPPLY

(75) Inventor: David W. Baarman, Fennville, MI (US)

(73) Assignee: Access Business Group International LLC, Ada, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/615,393

(22) Filed: Nov. 10, 2009

(65) Prior Publication Data

US 2010/0103702 A1  Apr. 29, 2010

Related U.S. Application Data

(63) Continuation of application No. 11/684,860, filed on Mar. 12, 2007, now Pat. No. 7,639,514, which is a continuation of application No. 10/689,499, filed on Oct. 20, 2003, now Pat. No. 7,212,414, and a continuation-in-part of application No. 10/175,095, filed on Jun. 18, 2002, now Pat. No. 6,673,250, which is a continuation-in-part of application No. 09/592,194, filed on Jun. 12, 2000, now Pat. No. 6,436,299.

(60) Provisional application No. 60/444,794, filed on Feb. 4, 2003, provisional application No. 60/140,090, filed on Jun. 21, 1999, provisional application No. 60/140,159, filed on Jun. 21, 1999.

(51) Int. Cl.
*H02J 13/00* (2006.01)
*A61L 2/10* (2006.01)
(Continued)

(52) U.S. Cl.
CPC ............... *H02J 13/0075* (2013.01); *A61L 2/10* (2013.01); *C02F 1/001* (2013.01); *C02F 1/008* (2013.01); *C02F 1/325* (2013.01); *C02F 9/005* (2013.01); *C02F 2201/3228* (2013.01); *C02F 2201/326* (2013.01); *C02F 2209/005* (2013.01); *C02F 2209/008* (2013.01); *C02F 2209/40* (2013.01); *H02J 5/005* (2013.01); *H02J 7/0027* (2013.01); *H02J 13/0086* (2013.01); *H02M 3/33523* (2013.01); *H02M 3/33569* (2013.01); *H02M 3/33576* (2013.01); *H02M 7/53803* (2013.01); *H02M 2007/4815* (2013.01); (Continued)

(58) Field of Classification Search
USPC ........ 363/16, 21.01, 39–41, 97, 131; 324/429
See application file for complete search history.

(56) References Cited

U.S. PATENT DOCUMENTS 3,590,382 A  6/1971  Kenney ............................. 381/3
3,949,268 A  4/1976  von Mangoldt
(Continued)

FOREIGN PATENT DOCUMENTS

DE  4233861  4/1994
EP  0178852  4/1986
(Continued)

OTHER PUBLICATIONS

Gulko, Michael, et al, Inductor-Controlled Current-Sourcing Resonant Inverter and its Application as a High Pressure Discharge Lamp Driver, IEEE, pp. 434-440, May 1994.
(Continued)

*Primary Examiner* — Jessica Han
(74) *Attorney, Agent, or Firm* — Warner Norcross & Judd LLP

(57) ABSTRACT

A contactless power supply has a dynamically configurable tank circuit powered by an inverter. The contactless power supply is inductively coupled to one or more loads. The inverter is connected to a DC power source. When loads are added or removed from the system, the contactless power supply is capable of modifying the resonant frequency of the tank circuit, the inverter frequency, the inverter duty cycle or the rail voltage of the DC power source.

34 Claims, 6 Drawing Sheets

(51) Int. Cl.
*C02F 1/32* (2006.01)
*C02F 9/00* (2006.01)
*H02J 5/00* (2006.01)
*H02M 3/335* (2006.01)
*H02M 7/538* (2007.01)
*H05B 37/03* (2006.01)
*H05B 41/36* (2006.01)
*C02F 1/00* (2006.01)
*H02J 7/00* (2006.01)
*H02M 7/48* (2006.01)

(52) U.S. Cl.
CPC ...... *H02M 2007/4818* (2013.01); *H05B 37/03* (2013.01); *H05B 41/36* (2013.01); *Y02B 70/1433* (2013.01); *Y02B 70/1441* (2013.01)

(56) References Cited

U.S. PATENT DOCUMENTS

| | | | | |
|---|---|---|---|---|
| 4,076,996 | A | 2/1978 | Maehara | |
| 4,639,714 | A | 1/1987 | Crowe | |
| 4,641,126 | A | 2/1987 | Crowe | |
| 4,644,321 | A | 2/1987 | Kennon | |
| 4,675,648 | A | 6/1987 | Roth et al. | |
| 4,800,328 | A | 1/1989 | Bolger et al. | |
| 4,818,855 | A | 4/1989 | Mongeon et al. | |
| 4,914,539 | A * | 4/1990 | Turner et al. | 361/18 |
| 5,070,293 | A | 12/1991 | Ishii et al. | 320/108 |
| 5,122,729 | A | 6/1992 | Itoga et al. | |
| 5,187,414 | A | 2/1993 | Fellows et al. | |
| 5,229,652 | A | 7/1993 | Hough | |
| 5,241,160 | A | 8/1993 | Bashan et al. | |
| 5,272,615 | A | 12/1993 | Wert | 363/41 |
| 5,298,836 | A | 3/1994 | Backmund et al. | |
| 5,325,046 | A | 6/1994 | Young et al. | |
| 5,341,280 | A | 8/1994 | Divan et al. | |
| 5,367,242 | A | 11/1994 | Hulman | |
| 5,406,174 | A | 4/1995 | Slegers | |
| 5,428,659 | A | 6/1995 | Renner et al. | |
| 5,440,300 | A | 8/1995 | Spillman, Jr. | |
| 5,446,346 | A | 8/1995 | Nilssen | |
| 5,450,305 | A | 9/1995 | Boys et al. | |
| 5,455,466 | A | 10/1995 | Parks | |
| 5,455,467 | A | 10/1995 | Young et al. | 307/104 |
| 5,476,488 | A | 12/1995 | Morgan et al. | |
| 5,495,405 | A | 2/1996 | Fujimura et al. | |
| 5,500,792 | A | 3/1996 | Jeon et al. | |
| 5,521,590 | A | 5/1996 | Hanaoka et al. | |
| 5,550,452 | A | 8/1996 | Shirai et al. | |
| 5,559,507 | A | 9/1996 | Beigel | |
| 5,586,017 | A | 12/1996 | Rohrbeck et al. | |
| 5,587,573 | A | 12/1996 | Owen et al. | |
| 5,596,567 | A | 1/1997 | deMuro | |
| 5,600,225 | A | 2/1997 | Goto | |
| 5,638,402 | A | 6/1997 | Osaka et al. | |
| 5,644,286 | A | 7/1997 | Brosh et al. | |
| 5,734,254 | A | 3/1998 | Stephens | |
| 5,757,144 | A | 5/1998 | Nilssen | |
| 5,777,861 | A | 7/1998 | Shimizu et al. | |
| 5,796,216 | A | 8/1998 | Beasley | 315/307 |
| 5,796,334 | A | 8/1998 | Chen | |
| 5,808,422 | A | 9/1998 | Venkitasubrahmanian et al. | 315/225 |
| 5,814,900 | A | 9/1998 | Esser et al. | |
| 5,818,127 | A | 10/1998 | Abraham | |
| 5,831,348 | A | 11/1998 | Nishizawa | 307/104 |
| 5,905,372 | A | 5/1999 | Kuffner et al. | |
| 5,917,429 | A | 6/1999 | Otis, Jr. et al. | |
| 5,929,604 | A | 7/1999 | Irvin | 320/136 |
| 5,963,012 | A | 10/1999 | Garcia | |
| 5,982,276 | A | 11/1999 | Stewart | |
| 5,982,764 | A | 11/1999 | Palermo et al. | |
| 5,983,076 | A | 11/1999 | Takasan et al. | 455/41.3 |
| 6,028,413 | A * | 2/2000 | Brockmann | 320/108 |
| 6,040,986 | A | 3/2000 | Sakamoto et al. | |
| 6,057,668 | A | 5/2000 | Chao | 320/108 |
| 6,072,362 | A | 6/2000 | Lincoln | |
| 6,118,249 | A | 9/2000 | Brockmann | |
| 6,127,799 | A | 10/2000 | Krishnan | |
| 6,141,227 | A | 10/2000 | Sheikh et al. | |
| 6,151,222 | A | 11/2000 | Barrett | |
| 6,157,258 | A | 12/2000 | Adishian et al. | |
| 6,173,899 | B1 | 1/2001 | Rozin | |
| 6,181,082 | B1 | 1/2001 | Moisin | |
| 6,184,651 | B1 | 2/2001 | Fernandez | |
| 6,191,537 | B1 | 2/2001 | Celso | |
| 6,211,799 | B1 | 4/2001 | Post et al. | |
| 6,212,430 | B1 | 4/2001 | Kung | |
| 6,252,380 | B1 | 6/2001 | Koenck | |
| 6,255,635 | B1 * | 7/2001 | Thompson et al. | 219/663 |
| 6,262,897 | B1 | 7/2001 | Yasumura | |
| 6,265,791 | B1 | 7/2001 | Eberl et al. | |
| 6,271,508 | B1 | 8/2001 | Thompson et al. | |
| 6,273,022 | B1 | 8/2001 | Pu et al. | |
| 6,301,128 | B1 | 10/2001 | Jang et al. | 363/17 |
| 6,307,468 | B1 | 10/2001 | Ward, Jr. | |
| 6,316,754 | B1 | 11/2001 | Schatz et al. | |
| 6,316,756 | B1 | 11/2001 | Thompson et al. | |
| 6,323,775 | B1 | 11/2001 | Hansson | |
| 6,348,679 | B1 | 2/2002 | Ryan et al. | |
| 6,359,267 | B1 | 3/2002 | Wilcox et al. | |
| 6,366,817 | B1 | 4/2002 | Kung | |
| 6,374,169 | B1 | 4/2002 | Demay et al. | 701/50 |
| 6,400,991 | B1 | 6/2002 | Kung | |
| 6,415,388 | B1 | 7/2002 | Browning et al. | 713/322 |
| 6,427,065 | B1 | 7/2002 | Suga et al. | |
| 6,429,622 | B1 | 8/2002 | Svensson | |
| 6,430,064 | B1 | 8/2002 | Tsuchimoto et al. | |
| 6,436,299 | B1 | 8/2002 | Baarman | |
| 6,437,521 | B1 | 8/2002 | Pienisaari | |
| 6,442,434 | B1 | 8/2002 | Zarinetchi et al. | |
| 6,452,482 | B1 | 9/2002 | Cern | |
| 6,462,432 | B1 | 10/2002 | Seelig et al. | |
| 6,472,827 | B1 | 10/2002 | Nilssen | |
| 6,498,456 | B2 | 12/2002 | Ettes et al. | |
| 6,504,318 | B1 | 1/2003 | Pienisaari | |
| 6,521,874 | B2 | 2/2003 | Thompson et al. | |
| 6,548,985 | B1 | 4/2003 | Hayes et al. | |
| 6,597,076 | B2 | 7/2003 | Scheible et al. | 307/104 |
| 6,600,142 | B2 | 7/2003 | Ryan et al. | |
| 6,615,023 | B1 | 9/2003 | Ehrensvärd | |
| 6,617,557 | B1 | 9/2003 | Ryan et al. | |
| 6,636,146 | B1 | 10/2003 | Wehoski | |
| 6,649,888 | B2 | 11/2003 | Ryan et al. | |
| 6,664,881 | B1 | 12/2003 | Thompson et al. | |
| 6,704,608 | B1 | 3/2004 | Azuma | 700/66 |
| 6,730,894 | B2 | 5/2004 | Thompson et al. | |
| 6,751,691 | B1 | 6/2004 | Douglas | 710/73 |
| 6,756,697 | B2 | 6/2004 | Mizutani et al. | 307/10.1 |
| 6,765,959 | B1 | 7/2004 | Tanaka et al. | |
| 6,812,445 | B2 | 11/2004 | Gorbold | |
| 6,825,620 | B2 | 11/2004 | Kuennen et al. | |
| 6,844,702 | B2 | 1/2005 | Giannopoulos et al. | |
| 6,861,629 | B2 | 3/2005 | Dahake et al. | |
| 6,906,495 | B2 | 6/2005 | Cheng et al. | 320/108 |
| 6,912,137 | B2 | 6/2005 | Berghegger | |
| 6,934,167 | B2 | 8/2005 | Jang | |
| 6,995,345 | B2 | 2/2006 | Gorbold | |
| 7,054,965 | B2 | 5/2006 | Bell et al. | 710/72 |
| 7,062,331 | B2 | 6/2006 | Zarinetchi et al. | |
| 7,065,658 | B2 | 6/2006 | Baraban et al. | |
| 7,110,269 | B2 | 9/2006 | Cao et al. | |
| 7,155,291 | B2 | 12/2006 | Zarinetchi et al. | |
| 7,212,414 | B2 | 5/2007 | Baarman | 363/16 |
| 7,489,530 | B2 | 2/2009 | Paull | |
| 7,522,878 | B2 * | 4/2009 | Baarman | 455/41.1 |
| 7,551,011 | B2 | 6/2009 | Paull | |
| 7,626,463 | B2 | 12/2009 | Paull | |
| 7,639,514 | B2 * | 12/2009 | Baarman | 363/16 |
| 7,804,045 | B2 | 9/2010 | Rosenbloom et al. | |
| 2001/0017781 | A1 | 8/2001 | Hideaki | |
| 2001/0052843 | A1 | 12/2001 | Wiesman et al. | |
| 2002/0017878 | A1 | 2/2002 | Hakuta et al. | |

(56) References Cited

U.S. PATENT DOCUMENTS

| | | |
|---|---|---|
| 2002/0082059 A1 | 6/2002 | Nariai et al. |
| 2002/0118004 A1 | 8/2002 | Scheible et al. |
| 2002/0130642 A1 | 9/2002 | Ettes et al. |
| 2002/0154518 A1 | 10/2002 | Elferich |
| 2003/0006880 A1 | 1/2003 | Zimmer |
| 2003/0015479 A1 | 1/2003 | Kuennen et al. |
| 2003/0030342 A1 | 2/2003 | Chen et al. ............... 310/102 R |
| 2003/0103039 A1 | 6/2003 | Burr et al. ..................... 345/163 |
| 2003/0210106 A1 | 11/2003 | Cheng |
| 2003/0214821 A1 | 11/2003 | Giannopoulos |
| 2004/0130915 A1 | 7/2004 | Baarman |
| 2004/0130916 A1 | 7/2004 | Baarman |
| 2004/0145342 A1 | 7/2004 | Lyon |
| 2005/0007067 A1 | 1/2005 | Baarman et al. |
| 2007/0109708 A1 | 5/2007 | Hussman et al. |
| 2008/0211478 A1 | 9/2008 | Hussman et al. |
| 2010/0171367 A1 | 7/2010 | Kitamura et al. |

FOREIGN PATENT DOCUMENTS

| | | |
|---|---|---|
| EP | 0267009 | 5/1988 |
| EP | 0558316 | 2/1993 |
| EP | 1096641 | 5/2001 |
| GB | 2124042 | 2/1984 |
| GB | 2 347 801 | 9/2000 |
| GB | 2388715 | 11/2003 |
| GB | 2388716 | 11/2003 |
| JP | 5978496 | 5/1984 |
| JP | 6196699 | 5/1986 |
| JP | 04183274 | 6/1992 |
| JP | H06-113478 | 4/1994 |
| JP | H06-133476 | 5/1994 |
| JP | 07153577 | 6/1995 |
| JP | 7507917 | 8/1995 |
| JP | 8506927 | 7/1996 |
| JP | H8-214473 | 8/1996 |
| JP | 8298778 | 11/1996 |
| JP | 09-103037 | 4/1997 |
| JP | H09-149565 | 6/1997 |
| JP | 09266081 | 10/1997 |
| JP | 10012197 | 1/1998 |
| JP | 10041089 | 2/1998 |
| JP | 10-225129 | 8/1998 |
| JP | H10-215530 | 8/1998 |
| JP | 10-258129 | 9/1998 |
| JP | 11188113 | 7/1999 |
| JP | H11-188113 | 7/1999 |
| JP | H11155245 | 7/1999 |
| JP | 2000-295796 | 10/2000 |
| JP | 2001-128375 | 5/2001 |
| JP | 2001-238372 | 8/2001 |
| JP | 2001238372 | 8/2001 |
| JP | 2003-018847 | 1/2003 |
| WO | 89/10030 | * 10/1989 |
| WO | 9419919 | 9/1994 |
| WO | 9422209 | 9/1994 |
| WO | 9428560 | 12/1994 |
| WO | 9605648 | 2/1996 |
| WO | 9617499 | 6/1996 |
| WO | WO 00/54387 | 9/2000 |
| WO | WO0054387 | 9/2000 |
| WO | 0078678 | 12/2000 |
| WO | WO00/54387 | 2/2001 |
| WO | 01/28629 | 4/2001 |
| WO | WO 01/80396 A1 | 10/2001 |
| WO | 02/37641 | 5/2002 |
| WO | WO 03/096361 | 11/2003 |

OTHER PUBLICATIONS

PCT International Search Report of PCT/US2004/001627, dated Jan. 22, 2004 and Written Opinion of PCT/US2004/0001627, dated Jan. 22, 2004.

PCT International Search Report of PCT/US2004/001758, dated Jan. 22, 2004 and Written Opinion of PCT/US2004/001758, dated Jan. 22, 2004.

U.S. Appl. No. 13/078,100, Office Action dated Nov. 23, 2011.

U.S. Appl. No. 13/078,100, Notice of Allowance and Fee(s) Due, and Office Action dated Mar. 6, 2012.

Current Control of Quantum Series Resonant Inverter and Application for a DC Motor Drive, Korea Advanced Institute of Science and Technology since 1971, Advisor: Myung Joong Youn by Gun-Woo Moon, Department of Electrical Engineering Korea Advanced Institute of Science and Technology, Dec. 28, 1991.

Malik E. Elbuluk, Member IEEE, George C. Verghese, member IEEE, and John G. Kassakian, Senior Member, IEEE, Sampled-Data Modeling and Digital Control of Resonant Converters, IEEE Transactions on Power Electronics, vol. 3, No. 3. Jul. 1988.

Gyu B. Joung, Chun T. Rim, and Gyu H. Cho, Integral Cycle Mode Control of the Series Resonant Converter, IEEE Transactions on Power Electronics, vol. 4, No. 1, Jan. 1989.

Japanese Office Action, Patent Application 2005-304983, Jun. 2, 2008.

Japanese Office Action, Patent Application 2005-304983, Apr. 22, 2009.

US 4,658,187, 04/1987, Grubbs (withdrawn)

* cited by examiner

ADAPTIVE INDUCTIVE POWER SUPPLY

RELATED APPLICATIONS

This application is a continuation of U.S. patent application Ser. No. 11/684,860, filed Mar. 12, 2007, which is a continuation of U.S. patent application Ser. No. 10/689,499, filed Oct. 20, 2003 (now U.S. Pat. No. 7,212,414). U.S. patent application Ser. No. 10/689,499 claims the benefit of U.S. Provisional Application Ser. No. 60/444,794, filed Feb. 4, 2003. U.S. patent application Ser. No. 10/689,499 is a continuation-in-part of U.S. patent application Ser. No. 10/175,095 entitled "Radio Frequency Identification System For a Fluid Treatment System," filed on Jun. 18, 2002 (now U.S. Pat. No. 6,673,250), which is a continuation-in-part of U.S. patent application Ser. No. 09/592,194 entitled Water Treatment System With an Inductively Coupled Ballast," filed Jun. 12, 2000 (now U.S. Pat. No. 6,436,299), which claims the benefit of 1) U.S. Provisional Patent Application Ser. No. 60/140,090 entitled "Point-of-Use-Water Treatment System," filed Jun. 21, 1999, and 2) U.S. Provisional Patent Application Ser. No. 60/140,159 entitled "Water Treatment System With an Inductively Coupled Ballast," filed Jun. 21, 1999.

This application incorporates by reference the following applications filed on the same date and assigned to the same assignee as this application: Adaptive Inductive Power Supply with Communication, Ser. No. 10/689,148; Inductive Coil Assembly, Ser. No. 10/689,244; Electrostatic Charge Storage Assembly, Ser. No. 10/689,154, and Adapter, Ser. No. 10/689,375.

BACKGROUND OF THE INVENTION

This invention relates generally to contactless power supplies, and more specifically to inductively coupled contactless power supplies.

Contactless energy transmission systems (CEETS) transfers electrical energy from one device to another without any mechanical connection. Because there is no mechanical connection, CEETS have many advantages over conventional energy systems. They are generally safer because there is little danger of sparks or electric shocks due to the isolation of the power supply. They also tend to have a longer life since there are no contacts to become worn. Due to these advantages, CEETS have been used in everything from toothbrushes to portable telephones to trains.

CEETS are composed of power supplies and remote devices. The remote devices could be chargeable, such as batteries, micro-capacitors, or any other chargeable energy source. Alternatively, CEETS could directly power the devices.

One kind of CEETS uses magnetic induction to transfer energy. Energy from a primary winding in the power supply is transferred inductively to a secondary winding in the chargeable device. Because the secondary winding is physically spaced from the primary winding, the inductive coupling occurs through the air.

Without a physical connection between the primary winding and the secondary winding, conventional feedback control is not present. Thus, control of the energy transfer in a CEETS from the primary to the secondary is difficult.

One common solution is to design a CEETS dedicated to one type of device. For example, a CEETS for a rechargeable toothbrush is designed only for recharging a toothbrush, while a CEETS for a rechargeable telephone works only with a specific type of telephone. While this solution allows the CEET to operate effectively with one particular device, it fails to be sufficiently flexible to allow the power supply to operate with different rechargeable devices.

Obviously, making a CEETS for each specific chargeable device is costly and inefficient. Thus, a system for contactless energy transmission which is efficient and can be used with a large variety of devices is highly desirable.

SUMMARY OF THE INVENTION

The aforementioned problems are overcome in the present invention.

A contactless power supply inductively couples by way of a tank circuit to a device. The power supply has a controller for dynamically adjusting the resonant frequency of the tank circuit. The tank circuit could have either a variable capacitor or a variable inductor, or both. In one embodiment, the power supply also may have an inverter. A drive circuit connected to the inverter controls the frequency of the inverter and the duty cycle of the inverter. A controller with an attached memory directs the operation of the inverter by way of the drive circuit. Alternatively, The inverter may also be connected to a DC power source. The controller could then change the rail voltage of the DC power source.

By altering the resonant frequency of the tank circuit, the frequency of the inverter, the duty cycle of the inverter and the rail voltage of the power supply, the contactless power supply can energize a variety of different devices. The power supply can even energize several different devices at the same time. This ability to power a multitude of different devices overcomes many of the limitations previously associated with CEETS. Further, because the power supply can energize a variety of different devices, a central single source for supply power to a variety of small electronic devices is possible.

In one embodiment, a sensor may also coupled to the tank circuit. It would monitor various operational characteristics of the tank circuit, such as the phase of the current within the tank circuit. These operation characteristics are indicative of the total load energized by the power supply. When the operational characteristics indicate that the power supply is not efficiently supplying power to the load, the controller causes the power supply to seek an improved configuration.

The process of seeking an improved configuration may include one or more of the following steps. The power supply could automatically attempt to compensate by changing the frequency of the inverter and the duty cycle of the inverter. If this sufficiently correct the efficiency of the power supply, the controller causes the tank circuit to change its resonant frequency. As is well known, the resonant frequency of a tank circuit is in fact a range centered about a frequency. The tank circuit will resonate at frequencies which are approximately the resonant frequency. However, the adaptive power supply described herein reconfigures the tank circuit to have a substantially different resonant frequency.

The tank circuit may consist of either a variable inductor or a variable capacitor or both. The controller would then change the inductance of the variable inductor or the capacitance of the variable capacitor, or both, thus causing the tank circuit to have a different resonant frequency.

The controller may also establish a new rail voltage for the DC power source. It also sets a new inverter frequency and a new duty cycle for the inverter. The adaptive power supply then operates with the new configuration.

If the adaptive power supply is still not operating effectively, the power supply will once again attempt to rectify the problem by changing the frequency of the inverter and the duty cycle of the inverter. If the problem is still not corrected, then the power supply will repeat the process of reconfiguring the tank circuit, setting a new inverter frequency and setting a new duty cycle.

This power supply continually searches for the most efficient settings to deliver power to the devices. However, if none of the various settings delivers power efficiently to the devices, then the power supply will select the most efficient of the previous configurations and operate the power supply with those settings.

Thus, the power supply efficiently powers a variety of loads. Further, because the power supply is contactless, a user does not need to have a multitude of different power supplies or connectors.

These and other objects, advantages and features of the invention will be more readily understood and appreciated by reference to the detailed description of the drawings.

DETAILED DESCRIPTION OF THE DRAWINGS

The present invention provides an adaptive inductive ballast circuit in which the inductance and/or the capacitance of the power supply circuit is variable to provide a broad range of adaptability, thereby permitting the ballast circuit to power a variety of inductively powered devices with widely differing load characteristics. For purposes of disclosure, the present invention is described in connection with a resonance-seeking ballast circuit, and more particularly in connection with the inductive ballast described in U.S. patent application Ser. No. 10/246,155 entitled "Inductively Coupled Ballast Circuit," which incorporated by reference into this application in its entirety. The present invention is, however, well suited for use with other inductive ballast circuits.

Figure 1:
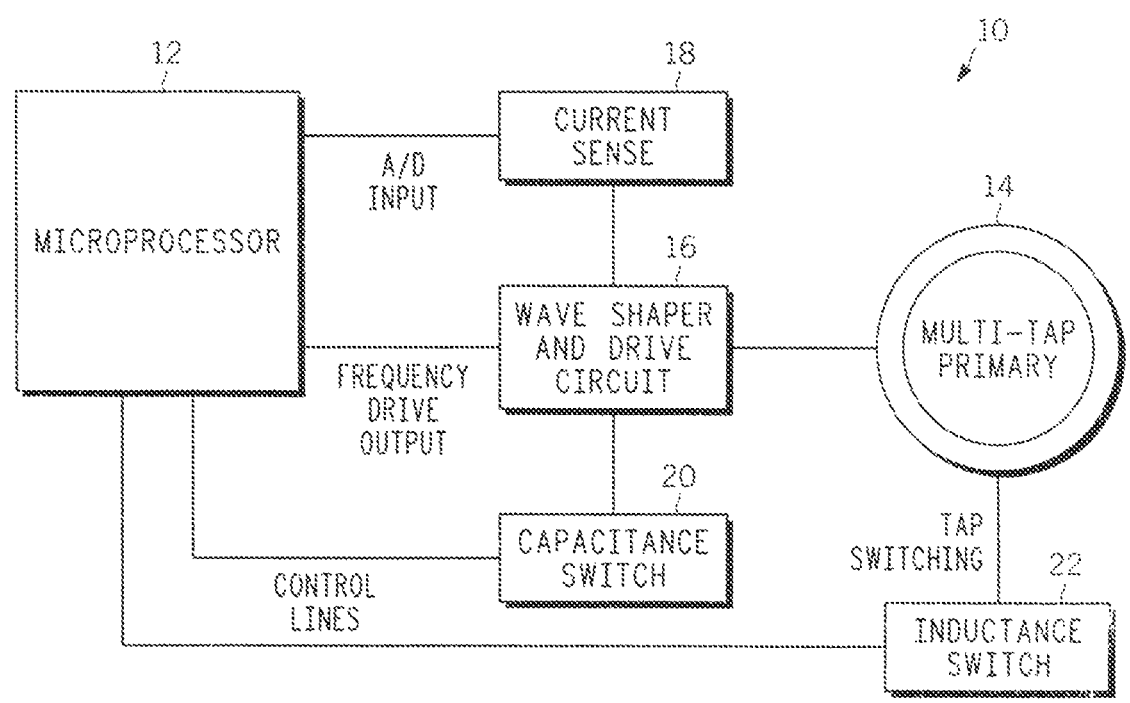
FIG. 1 is a block diagram of an adaptive inductive ballast in accordance with one embodiment of the present invention.

A block diagram showing the general construction of an adaptive inductive ballast 10 in accordance with one embodiment of the present invention is shown in FIG. 1. As illustrated, the adaptive inductive ballast 10 generally includes a microprocessor 12 that controls operation of the circuit, a multi-tap primary 14 for generating a magnetic field, a wave shaper and drive subcircuit 16 that generates the signal applied to the primary 14, a current sense subcircuit 18 that monitors the signal applied to the primary 14 and provides corresponding feedback to the microprocessor 12, a capacitance switch 20 for adjusting the capacitance values in the wave shaper and drive subcircuit 16, and an inductance switch 22 for adjusting the inductance of the multi-tap primary 14. The microprocessor is a conventional microprocessor widely available from a variety of suppliers.

The capacitance switch 20 generally includes two banks of capacitors and a plurality of switches, such as transistors, that are selectively actuatable by the microprocessor 12 to control the values of the two capacitor banks. The capacitors in each bank can be arranged in series or parallel depending on the desired range and distribution of possible capacitance values. The first bank of capacitors replace capacitor 271 of the pre-existing resonance-seeking ballast shown in the above referenced application. Similarly, the second back of capacitors replace capacitor 272 of the pre-existing resonance-seeking ballast shown in the above referenced patent application. In effect, the capacitance switch 20 makes capacitors 271 and 272 from the pre-existing resonance-seeking ballast into variable capacitors, the values of which are controlled by the microprocessor 12. Alternatively, the described capacitance switch 20 can be replaced by other circuitry capable of providing variable capacitance.

The inductance switch 22 generally includes a multi-tap primary 14 and a plurality of switches, such as transistors, that are selectively actuatable by the microprocessor 12 to control the values of the inductance of the primary 14. The multi-tap primary 14 replaces primary 270 of the pre-existing resonance-seeking ballast shown in the attached patent application. In effect, the inductance switch 22 makes primary 270 from the pre-existing resonance-seeking ballast into a variable inductance coil by varying the number of turns in the primary 14, the value of which is controlled by the microprocessor 12. Alternatively, the described inductance switch 22 can be replaced by other circuitry capable of providing variable inductance.

In general operation, the microprocessor 12 is programmed to receive input from the current sense subcircuit 18, which is indicative of the current applied to the primary 14. The microprocessor 12 is programmed to separately adjust the capacitance switch 20 and the inductance switch 22 to cycle through the range of capacitance values and inductance values available to the circuit. The microprocessor 12 continues to monitor the input from the current sense circuit 18 while adjusting the capacitance and inductance values to determine which values provide optimum current to the primary 14. The microprocessor 12 then locks the adaptive ballast into the optimum settings.

Figure 2:
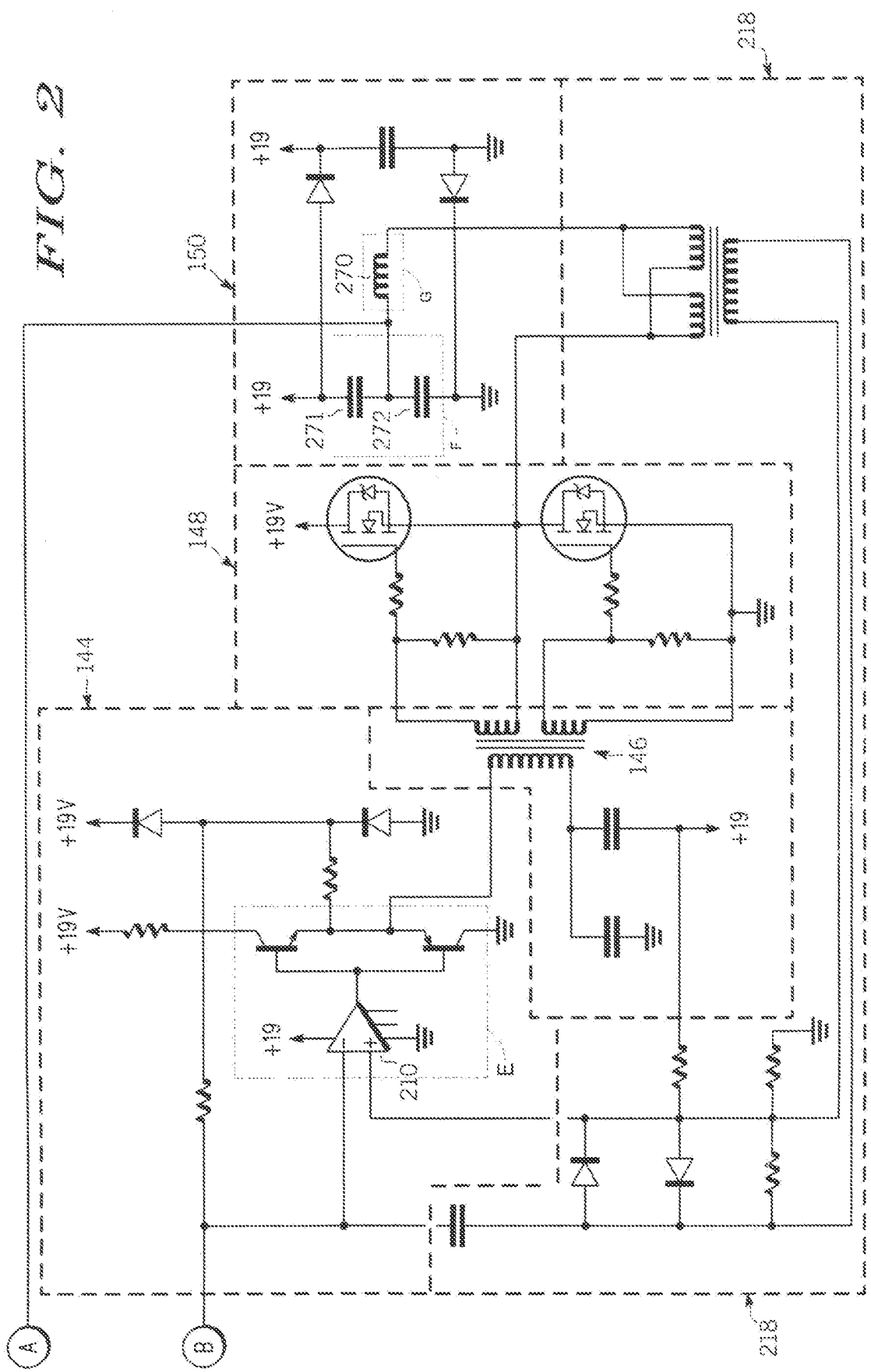
FIG. 2 is a schematic diagram of the resonance-seeking ballast of the attached patent application marked to show changes to incorporate the adaptive inductive ballast of the present invention.

Some of the changes required to adapt the resonance-seeking inductive ballast of the application patent application into an embodiment of the adaptive inductive ballast circuit 10 are noted in the schematic diagram of FIG. 2.

While the pre-existing resonance-seeking ballast is described in greater detail in U.S. patent application Ser. No. 10/246,155, an overview of the circuit may be helpful to a fuller understanding of this invention. A ballast feedback circuit is connected at point A and a control circuit is connected at point B. Oscillator 144 provides half bridge inverter 148 with an alternating signal by way of drive 146. Half bridge inverter powers tank circuit 150. Current sensing circuit 218 provides feedback to oscillator 144. The feedback circuit, control circuit, oscillator, half bridge inverter, drive and current sensing circuit 218 as well as other supporting circuitry is more fully described in the above referenced patent application.

In FIG. 2, a phase delay could be inserted at E and can be controlled as a delay line or even DSP (Digital Signal Processing) could be used to delay this signal. This delay can be used to throttle the phase and control secondary amplitude. At F, switched capacitance can adjust the resonant frequency based on the adjustable primary inductance. Simple transistors can be used to switch in and out capacitance. The capacitance is changed when the primary inductor changes as to match load. At G, primary inductance can be switched to adjust the power required by the secondary circuit. With that load information, the control processor can adjust the inductance as needed to provide the power required. The inductance can be switched using transistors and multiple taps from the primary inductor controlled by the microprocessor.

Figure 3:
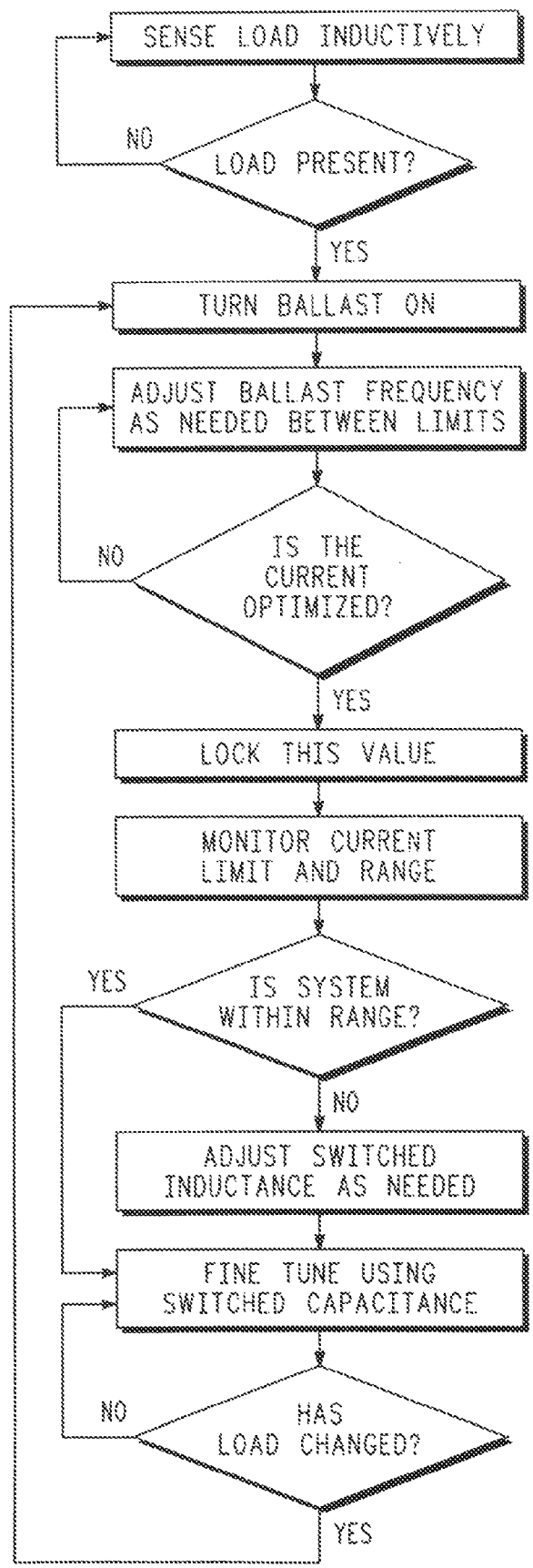
FIG. 3 is a flow chart illustrating operation of the adaptive inductive ballast.

The operating sequence of the adaptive inductive ballast circuit is described in more detail in connection with FIG. 3. In operation, the illustrated system waits until it determines that a load is present before applying power to the primary 14. This will save power and may be done by providing each inductively powered device with a magnet that actuates a reed switch adjacent to the primary. Alternatively, a user-actuated switch (not shown) may be provided so that the user can engage the power supply when an inductively powered device is present. As another alternative, the inductively powered device may be configured to mechanically actuate a switch when it is placed into located by the primary to signal its presence. As a further alternative, the switching mechanism can be eliminated and the ballast circuit can provide power to the primary 14 regardless of the presence of a load.

Once the power supply circuit is activated, the circuit adjusts its frequency to optimize the current applied to the primary. After the appropriate operating frequency has been determined at initial capacitance and inductance values, the microprocessor locks the ballast circuit into the operating frequency and then begins to cycle through the range of inductance values available through the multi-tap primary. After each change in inductance value, the microprocessor unlocks the operating frequency and permits the ballast circuit to seek resonance, settling at a frequency that provides optimal current to the primary. The microprocessor continues cycling through the available inductance values until it has determined which value provides optimal current to the primary. In one embodiment, a progressive scanning process is used to determine the appropriate inductance value. This is achieved by starting the scanning process with the lowest inductance value, and sequentially stepping up the inductance value until the change in inductance value results in a reduction in the current applied to the primary. The microprocessor will then step back down one inductance value, where the greatest current was achieved. Alternatively, the scanning process may begin with the highest inductance value, and sequentially step down the inductance value until the change in inductance value results in a reduction in the current applied to the primary. The microprocessor will then step back up one inductance value, where the greatest current was achieved. As another alternative, the microprocessor can step through each inductance value to determine the corresponding current, and after stepping through each value, return to the inductance value that provided the greatest current to the primary.

After the appropriate inductance value is determined, the microprocessor locks the circuit at the determined inductance value and begins to cycle through the capacitance values. In one embodiment, the microprocessor uses a progressive scanning technique to determine the capacitance that provides the primary with the greatest current. The scanning process may progress upwardly from the lowest capacitance value or downwardly from the highest capacitance value, as described above in connection with the scanning process for the inductance value. As an alternative to a progressive scanning process, the microprocessor can step through each capacitance value to determine the corresponding current, and after stepping through each value, return to the capacitance value that provided the greatest current to the primary.

In this embodiment, the frequency of the ballast circuit is not permitted to vary once the appropriate inductance value has been determined. The microprocessor can, alternatively, be programmed to permit the ballast circuit to seek resonance after each change in capacitance value.

In an alternative embodiment, the microprocessor may be programmed to provide adjustment of only the capacitance value or only the inductance value of the power supply circuit. In the former alternative, the multi-tap primary can be replaced by a conventional single-tap primary and the inductance switch can be eliminated. In the latter alternative, the capacitor bank can be replaced by a single set of capacitors and the capacitance switch can be eliminated. In another alternative embodiment, the microprocessor can be programmed to adjust the capacitance before adjusting the inductance.

As noted above, the present invention is not limited to use in connection with a resonance-seeking ballast. In other applications, a current sensor may be incorporated into the ballast to provide input to the microprocessor that is representative of the current being applied to the primary. In operation without a resonance-seeking ballast, the microprocessor will separately cycle through the various capacitance and inductance values to determine the values that provide optimum power to the primary.

In a further alternative embodiment, the adaptive inductive ballast 10 may include phase delay circuitry (not shown) that permits the ballast 10 to throttle the phase and control secondary amplitude. The phase delay circuitry may include a delay line or a Digital Signal Processor (DSP) that is connected to the wave shaper and drive circuit 16 following the operational amplifier 210.

Figure 4:
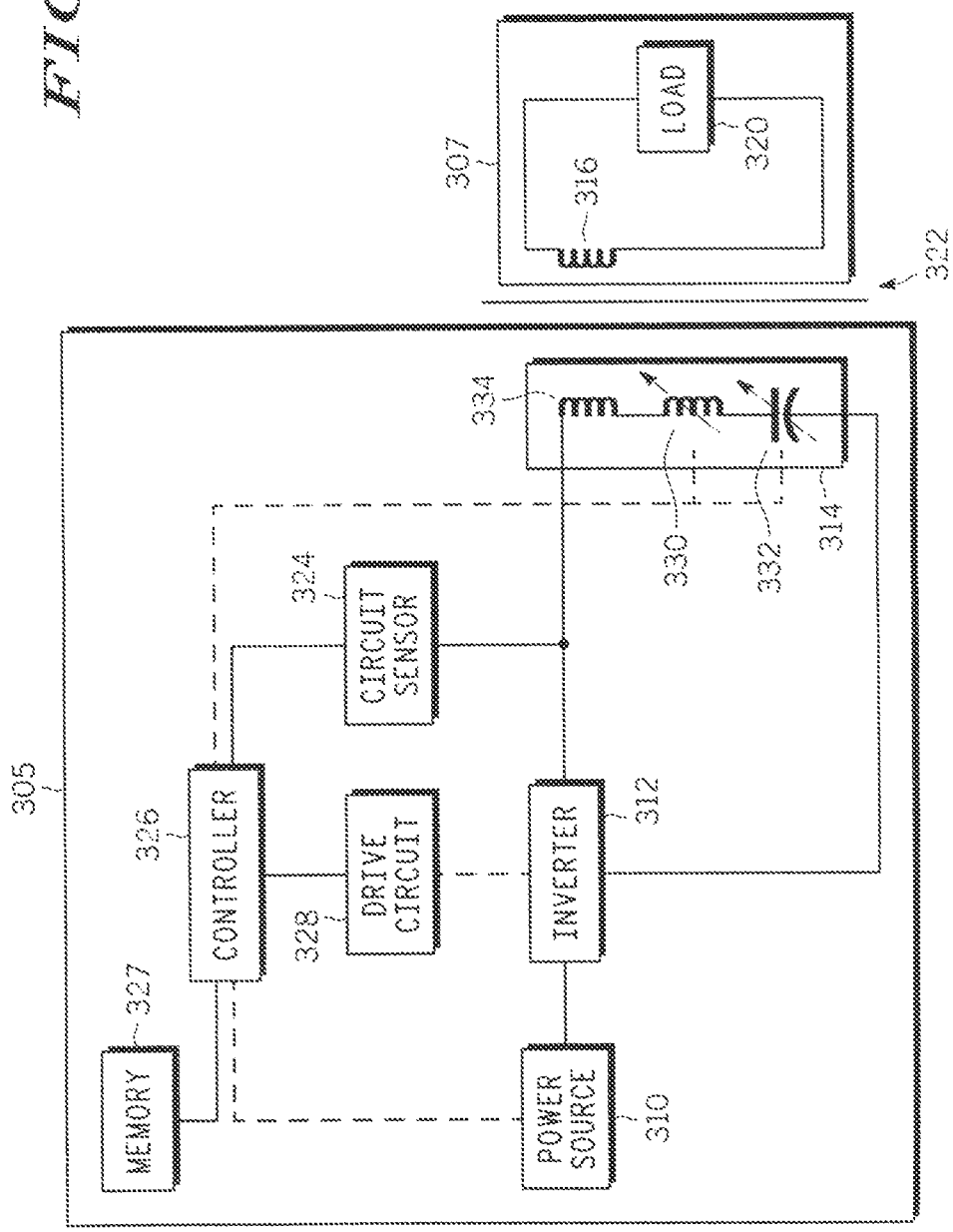
FIG. 4 is a block diagram for an adaptive contactless energy transmission system.

Further exemplifying the ideas and concepts expressed above, an additional embodiment for an adaptive contactless energy transmission system is shown in the block diagram of FIG. 4. The adaptive contactless energy transmission system is comprised of adaptive inductive power supply 305 and remote device 307.

As is well know, power source 310 is a DC power source providing DC (direct current) power to inverter 312. Inverter 312 converts the DC power to AC (alternating current) power. Inverter 312 acts as an AC power source supplying the AC power to tank circuit 314. Tank circuit 314 is inductively coupled to secondary winding 316 of remote device 307.

Secondary winding 316 of remote device 307 has no core. Line 322 indicates an air gap between remote device 307 and adaptive inductive power supply 305.

Remote device 307 has a load 320. Load 320 could include a rechargeable device, such as a micro-capacitor or a rechargeable battery. Alternatively, load 320 could be a lamp, radio or any other electrical device adapted to receive power from adaptive inductive power supply 305 whenever remote device 307 is placed in proximity of adaptive inductive power supply 305.

Circuit sensor 324 is coupled to the tank circuit 314 and inverter 312. Circuit sensor 324 is also coupled to controller 326. Circuit sensor 324 provides information regarding the operational parameters of adaptive inductive power supply 305. For example, circuit sensor 324 could be a current sensor used to provide controller 326 information regarding the phase, frequency and amplitude of the current in tank circuit 314.

Controller 326 could be any one of a multitude of commonly available microcontrollers programmed to perform the functions hereinafter described, such as the Intel 8051 or the Motorola 6811, or any of the many variants of those microcontrollers. Controller 326 could have a ROM (read only memory) and RAM (random access memory) on the chip. Controller 326 could have a series of analog and digital outputs for controlling the various functions within the adaptive inductive power supply.

Controller 326 is connected to memory 327. Controller 326 is also coupled to drive circuit 328. Drive circuit 328 regulates the operation of inverter 312, such as the frequency and timing of inverter 312. Drive circuit 328 could be constructed in a number of different manners. For example, driver circuit 328 could be constructed of discrete components such as transistors, resistors and capacitors; it could be a discrete integrated circuit designed to drive inverters; or it could be a functional component of controller 326 if controller 326 were a microcontroller.

Controller 326 is also coupled to power source 310. Controller 326 can manipulate the rail voltage of power source 310. As is well known, by altering the rail voltage of power source 310, the amplitude of the output of inverter 312 is also altered.

Finally, controller 326 is coupled to variable inductor 330 and variable capacitor 332 of tank circuit 314. Controller 326 could be a microcontroller, such as an 8051-type microcontroller. Alternatively, controller 326 could be a microprocessor with additional supporting circuitry.

Controller 326 can modify the inductance of variable inductor 330 or the capacitance of variable capacitor 332. This could be done, e.g., by switching in or out additional capacitor or inductors or by changing the physical characteristics of variable inductor 330 or variable capacitor 332. By modifying the inductance of variable inductor 330 and the capacitance of variable capacitor 332, the resonant frequency of tank circuit 314 can be changed.

By modifying the inductance of variable inductor 330 or the capacitance of variable capacitor 332, or both, tank circuit 314 may have a first resonant frequency and a second resonant frequency. Tank circuit 314 could also have several resonant frequencies. As used herein, the term "resonant frequency" refers to a band of frequencies within which tank circuit 314 will resonate. As is well known, a tank circuit will have a resonant frequency, but will continue to resonate within a range of frequencies.

Variable inductor 330 could be a thyristor controlled variable inductor, a compressible variable inductor, parallel laminated core variable inductor, a series of inductors and switches capable of placing select fixed inductors into tank circuit 314, or any other controllable variable inductor. Variable capacitor 332 could be a switched capacitor array, a series of fixed capacitors and switches capable of placing select fixed capacitors into tank circuit 314, or any other controllable variable capacitor.

Tank circuit 314 also includes primary winding 334. Primary winding 334 and variable inductor 330 are shown separate. Alternatively, primary winding 334 and variable inductor 330 could be combined into a single element.

Tank circuit 314 is shown as a series resonant tank circuit. A parallel resonant tank circuit could also be used.

Figure 5A:
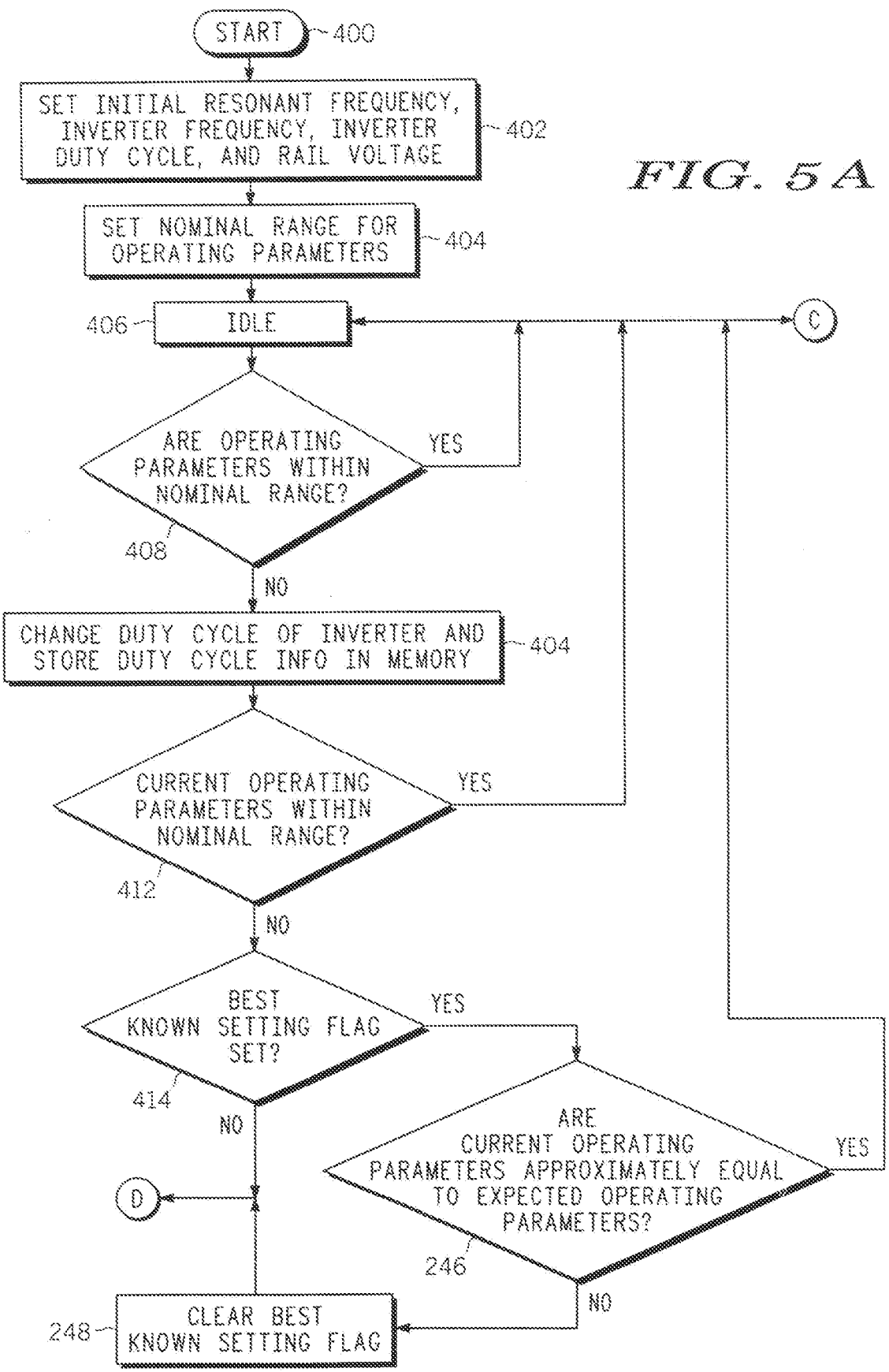
FIGS. 5A and 5B are a flow chart showing the operating of an adaptive contactless energy transmission system.
Figure 5B:
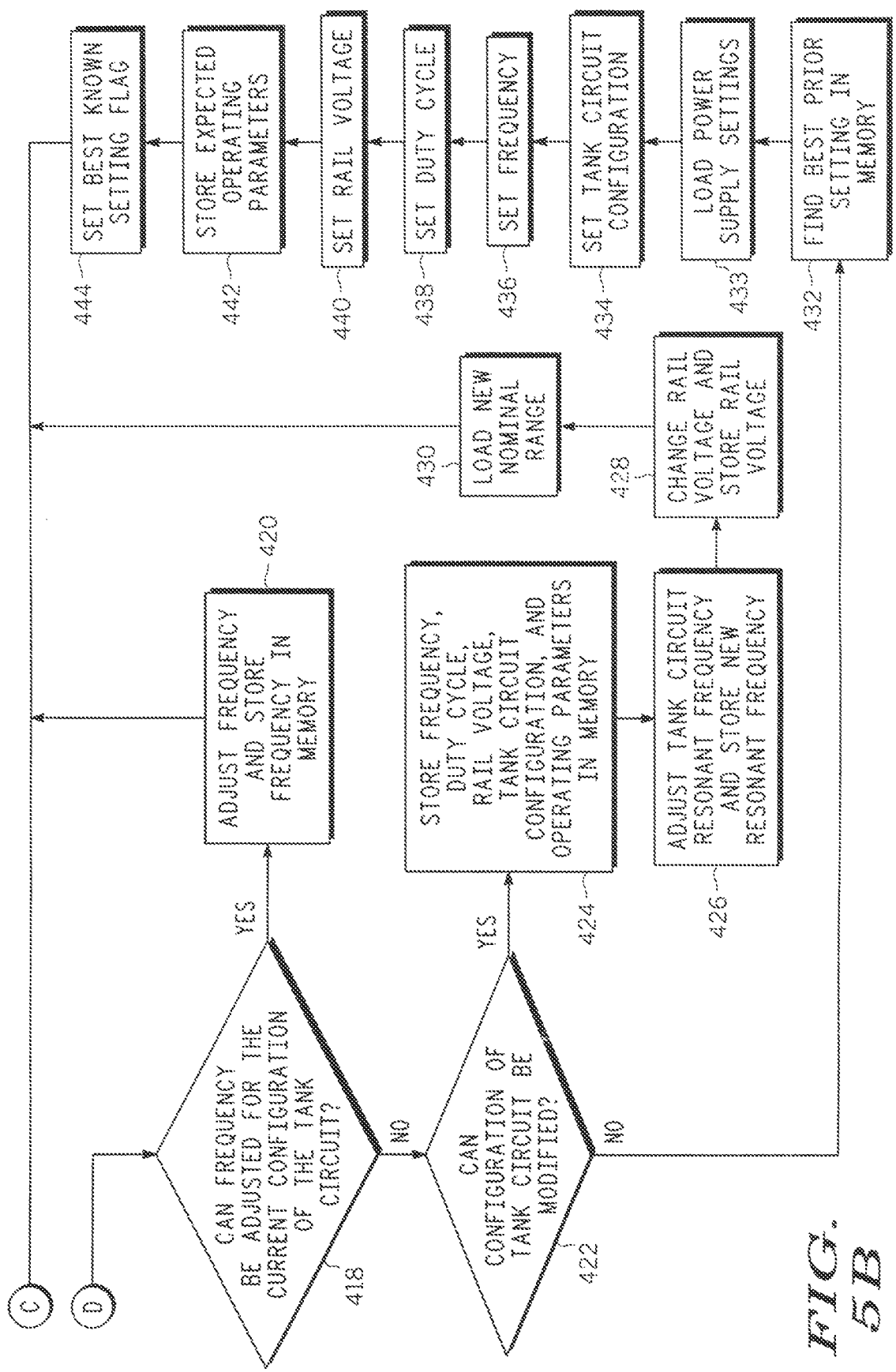

FIGS. 5A and 5B show a flow chart showing the operation of adaptive inductive power supply 305 of adaptive contactless energy transmission system shown in FIG. 4.

When turned on (step 400), controller 326 initializes the resonant frequency of tank circuit 314 by setting the inductance of variable inductor 330 and the capacitance variable capacitor 332 so that tank circuit 314 operates at a pre-selected initial resonant frequency. Step 402. Controller 326 initializes drive circuit 328 to operate at a pre-selected frequency with a pre-selected phase offset. Controller 326 initializes power source 310 to operate at a predetermined rail voltage. Step 402.

In order to conserve power, when adaptive inductive power supply 305 is initially energized, adaptive inductive power supply 305 might be initialized to supply power at a very low level. Alternatively, adaptive inductive power supply 305 might be initialized to supply power at a more moderate level to accommodate some common remote devices.

Controller 326 then sets the nominal range for the operating parameters. Step 404. The operating parameters for the power supply are various measures of current and voltage throughout the system. For example, the peak to peak inverter voltage, the RMS current flowing through the primary winding, and the phase offset of the current flowing through the primary winding are all operating parameters. For example, the operating range could include a range of the phase offset between the inverter voltage and the voltage current, a range for the current amplitude, and a range for the inverter output voltage. As a further example, an operating range could be an inverter voltage from 5 Volts to 5.3 volts, with a current phase offset of no more than 20 degrees, and a current amplitude of between ½ and 1 amp.

The nominal range is the acceptable range of possible values for the operating parameters. If an operating parameter are not within the nominal range, then the power supply is not operating efficiently.

Returning to FIG. 5, the system then idles. Step 406. Controller 326 continually monitors the operating parameters of adaptive inductive power supply 305. If the operating parameters fall within the nominal range, then the circuit continues to idle. Step 408.

When remote device 307 is placed near primary winding 334, then power is drawn from adaptive inductive power supply 305. As a result, the operating parameters change. If the operating parameters fall outside of the nominal range, then controller 326 reconfigures adaptive inductive power supply 305.

If adaptive inductive power supply 305 had an initially low power setting, adaptive inductive power supply 305 would thus sense the presence of the remote device, and automatically increase power to a more moderate level.

Obviously, reconfiguration of adaptive inductive power supply 305 could be triggered by one operating parameter falling outside of the nominal range, or reconfiguration of adaptive inductive power supply 305 could be triggered by a combination of operating parameters falling outside of the nominal range. It is satisfactory to monitor only the phase of the current flowing through the primary winding. However, various enhancements where other operating parameters are measured and weighted together could be readily conceived.

First, controller 326 causes drive circuit 328 to alter the duty cycle of inverter 312. Step 410. The duty cycle of inverter 312 is altered, and the altered duty cycle is stored in memory 327.

The operating parameters are again measured. Step 412. If the operating parameters are still outside of the nominal range, then a 'best known setting' flag is checked. Step 414. The 'best known setting' flag is discussed below.

If the "best know setting flag" is not set, then controller 326 determines whether the inverter frequency can be adjusted and still maintain resonance within tank circuit 314. Step 418. Controller 326 first finds the maximum and minimum resonant frequency of tank circuit 314.

The maximum and minimum resonant frequency of tank circuit 314 for any particular configuration of variable inductor 330 and variable capacitor 332 could be stored in memory 327. In the alternative, the maximum and minimum resonant frequency of tank circuit 314 could be calculated from the inductance of primary winding 334, the inductance of variable inductor 330, and the capacitance of variable capacitor 332. Controller 326 then compares the maximum and minimum resonant frequency of tank circuit 314 with the current operating frequency of inverter 312.

If possible, then controller 326 causes drive circuit 328 to adjust the inverter frequency and stores the new inverter frequency in memory 327. Step 420. The circuit returns to the idle state. Step 406. If the inverter frequency cannot be adjusted within the resonant frequency of the current configuration of tank circuit 314, then controller 326 determines whether the configuration of tank circuit 314 can be modified. Step 422.

If it can be modified, then controller 326 stores the current frequency, duty cycle, rail voltage, tank circuit configuration, and operating parameters in memory 327. Step 424. It then adjust the tank circuit resonant frequency. Step 426. Adjustment of the tank circuit resonant frequency is accomplished by changing the inductance of variable inductor 330 and the capacitance of variable capacitor 332.

The rail voltage could then be changed. Step 428. Since the resonant frequency of tank circuit 314 has been altered, a new nominal range for the operating parameters is calculated or loaded from memory 327. Step 430. The power supply then returns to idle. Step 406.

If the configuration of tank circuit 314 can not be further modified, then controller 326 searches for the best prior configuration. Step 432. Controller 326 compares the operating parameters previously stored and selects the best configuration.

After selecting the best configuration, controller 326 retrieves various settings of adaptive inductive power supply 305 from memory for that configuration. Step 433. Controller 326 then sets the configuration of tank circuit 314 by setting the inductance of adjustable inductor 30 and capacitance of adjustable capacitor 32. Step 434. Controller 326 then sets the frequency of inverter 312. Step 436. Controller 326 then sets the duty cycle of inverter 312. Step 438. Controller 326 sets the rail voltage of power source 310. Step 440.

Controller 326 then stores the expected operating parameters in memory 327. Step 442. Alternatively, controller 326 could set a pointer to the expecting operating parameters in memory 327. Controller 326 then sets the 'best known setting' flag. Step 444. The power supply then returns to the idle state. Step 406. The 'best known setting' flag is an indication to controller 326 that the current settings being used by adaptive inductive power supply 305 are the best available.

If the 'best known setting' flag is set, then the system is operating at its best settings even though the operating parameters are outside of the nominal range. Further changes to the inverter frequency, resonant circuit frequency, inverter duty cycle or rail voltage thus would not result in any improvement to the system. With the 'best known setting' flag set, the system checks if the operating parameters are approximately equal to the expected operating parameters.

Thus, if the best known setting flag is set (See Step 414), controller 326 checks whether the current operating parameters are approximately the same as the expected operating parameters. Step 446. If so, then further adjustments to power supply will not result in any improved performance, and therefore the system merely returns to the idle state. Step 406.

If, on the other hand, the current operating parameters are not approximately equal to the expected operating parameters, then the best known setting flag is cleared. Step 448. The process of reconfiguring adaptive inductive power supply 305 continues. Step 422.

The adaptive contactless energy transmission system described thus can dynamically handle a variety of different devices. Adaptive inductive power supply 305 automatically adjusts to different devices with different loads, and continually determines and optimal operating configuration for the power supply.

Further, more than a single device can be simultaneously powered by adaptive inductive power supply 305. As new devices are placed near adaptive inductive power supply 305, controller 326 continually adjusts the operating parameters of adaptive inductive power supply 305 to maintain efficiency. This allows for one single power supply to provide power to a multitude of different devices. The devices need not be located immediately adjacent adaptive inductive power supply 305. That can be spaced at different distances away from adaptive inductive power supply 305. For example, it is possible to construct a power supply whereby sealed lights are stacked near adaptive inductive power supply 305 and each light will be illuminated even though the distance from adaptive inductive power supply 305 is different for each light.

The above description is of the preferred embodiment. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The invention claimed is:

1. A contactless power supply for supplying power wirelessly to a remote device having a secondary inductor in electrical communication with a load, said contactless power supply comprising:
   a tank circuit having a primary inductor for transferring power to said remote device having said secondary inductor in electrical communication with said load, by an inductive coupling, wherein a resonant frequency of said tank circuit is based at least in part on the load;
   circuitry for applying power at a rail voltage to said tank circuit, said circuitry applying said power at an operating frequency and a duty cycle; and
   a controller coupled to said circuitry, said controller configured to monitor at least one operational characteristic of the contactless power supply, said controller configured to actively vary, based on said at least one operational characteristic, said operating frequency of said power from a first operating frequency to a second operating frequency;
   wherein said controller is configured to actively vary said resonant frequency during operation such that said resonant frequency changes from a first resonant frequency to a second resonant frequency, wherein said first operating frequency is at or near said first resonant frequency, and wherein said second operating frequency is at or near said second resonant frequency.

2. The contactless power supply of claim 1 wherein said controller is configured to vary at least three of said resonant frequency of said tank circuit, said operating frequency of said power, said duty cycle of said power and said rail voltage of said power.

3. The contactless power supply of claim 1 wherein said controller is configured to vary said resonant frequency of said tank circuit, said operating frequency of said power, said duty cycle of said power and said rail voltage of said power.

4. The contactless power supply of claim 1 wherein said controller is configured to vary said duty cycle of said power.

5. The contactless power supply of claim 1 wherein said controller is configured to vary said rail voltage of said power.

6. The contactless power supply of claim 1 further including a circuit sensor coupled to said tank circuit and to said controller, said circuit sensor providing said controller with an input indicative of a characteristic of power in said tank circuit; and
wherein said controller is configured to vary said resonant frequency of said tank circuit and said operating frequency of said power as a function of said input indicative of a characteristic of power in said resonant circuit.

7. The contactless power supply of claim 1 wherein said controller is configured to monitor said at least one operational characteristic of the contactless power supply to determine if the contactless power supply is operating effectively, wherein said controller is configured to store in memory a best known setting based on said determination, said controller configured to reconfigure the contactless power supply upon a determination that the contactless power supply is not operating effectively and based on the best known setting.

8. A contactless power supply system comprising:
an inductive power supply having at least one operating parameter, said inductive power supply having a resonant frequency, an operating frequency, a rail voltage and a duty cycle;
a remote device having a secondary inductor in electrical communication with a load, said remote device capable of inductively receiving power from said power supply via an inductive coupling when placed within sufficient proximity to said inductive power supply, said remote device capable of affecting said at least one operating parameter when placed within sufficient proximity to said inductive power supply; and
wherein said power supply includes:
a tank circuit having a primary inductor for inductively transferring power to said remote device; and
a controller programmed to actively adjust, during operation, said operating frequency such that said operating frequency is controlled to be at or near said resonant frequency, said controller programmed to continually monitor said at least one operating parameter of said power supply while actively controlling said operating frequency
wherein said controller is programmed to reconfigure the power supply, based on said at least one operating parameter falling outside a nominal range while actively controlling said operating frequency, by actively adjusting said resonant frequency.

9. The contactless power supply system of claim 8 further including a circuit sensor coupled to said resonant circuit and to said controller, said circuit sensor providing said controller with an input indicative of a characteristic of power in said resonant circuit.

10. The contactless power supply of claim 9 wherein said controller is configured to actively vary said resonant frequency of the power supply and said operating frequency of the power supply as a function of said input indicative of a characteristic of power in said resonant circuit.

11. The contactless power supply system of claim 8 wherein said controller is configured to vary at least three of a rail voltage of said resonant frequency, said operating frequency, said duty cycle and said rail voltage.

12. The contactless power supply system of claim 8 wherein said controller is configured to vary said resonant frequency, said operating frequency, said rail voltage and said duty cycle.

13. The contactless power supply system of claim 8 wherein said controller is configured to actively adjust said duty cycle.

14. The contactless power supply system of claim 8 wherein said controller is configured to actively adjust said rail voltage.

15. The contactless power supply system of claim 8 further including a circuit sensor coupled to said controller, said circuit sensor providing said controller with an input indicative of a characteristic of power in the power supply; and
wherein said controller is configured to vary said resonant frequency and said operating frequency.

16. The contactless power supply system of claim 8 wherein said circuit sensor is a current sensor.

17. The contactless power supply system of claim 8 wherein said controller is configured to actively adjust said rail voltage.

18. The contactless power supply system of claim 8 wherein said inductive power supply includes at least one of a variable capacitor and a variable inductor, wherein said controller is configured to actively vary at least one of a variable capacitor and a variable inductor to adjust said resonant frequency.

19. A method of operating an inductive power supply for a remote device having a secondary inductor in electrical communication with a load, the method including the steps of:
applying power to a tank circuit within the inductive power supply;
establishing an inductive coupling between the inductive power supply and the remote device having the secondary inductor in electrical communication with said load;
monitoring at least one operating parameter of the inductive power supply after establishing the inductive coupling;
based upon said monitoring step, reconfiguring the inductive power supply by:
actively adjusting, based on an operating parameter, an impedance of the tank circuit to affect a variable resonant frequency; and
actively adjusting a variable operating frequency of power applied to the tank circuit such that the variable operating frequency is at or near the variable resonant frequency, wherein actively adjusting the variable operating frequency affects said operating parameter based on which said impedance of the tank circuit is adjusted.

20. The method of claim 19 wherein said monitoring step is further defined as sensing a characteristic of power in the power supply.

21. The method of claim 20 wherein said sensing step is further defined as sensing current in the tank circuit.

22. The method of claim 19 further comprising adjusting a rail voltage of the power applied to the tank circuit.

23. The method of claim 19 wherein said actively adjusting the impedance of the tank circuit to affect the variable resonant frequency includes repeatedly adjusting the variable resonant frequency until the operating parameter is at a best known setting.

24. The method of claim 23 wherein said actively adjusting the variable operating frequency includes repeatedly adjusting the variable operating frequency until the operating parameter is at a best known setting.

25. The method of claim 19 wherein said step of reconfiguring the inductive power supply further includes:
adjusting a first characteristic of the power supply, the first characteristic being one of the rail voltage of the power applied to the tank circuit or the duty cycle of the power applied to the tank circuit.

26. The method of claim 25 wherein said step of reconfiguring the inductive power supply further includes:

adjusting a second characteristic of the power supply, the second characteristic being one of the rail voltage of the power applied to the tank circuit, or the duty cycle of the power applied to the tank circuit and being different from the first characteristic.

27. A method for controlling operation of an inductive power supply system, comprising the steps of:
    establishing an inductive coupling between an inductive power supply and a remote device having a secondary inductor in electrical communication with a load, the inductive power supply having a controller and a tank circuit, wherein a resonant frequency of said tank circuit is based at least in part on the load;
    actively adjusting, based on a setting retrieved from memory, a resonant frequency of the inductive power supply when the remote device is inductively coupled with the inductive power supply;
    actively adjusting an operating frequency of the inductive power supply such that said operating frequency is at or near the resonant frequency.

28. The method of claim 27 further comprising repeating said step of actively adjusting said operating frequency of the inductive power supply in response to active adjustments of said resonant frequency in the inductive power supply during operation of the inductive power supply.

29. The method of claim 27 further comprising detecting an operating parameter of the tank circuit; and determining whether the operational parameter of the tank circuit in the inductive power supply on the primary side is within a nominal range, wherein said adjusting is in response to determining that said operational parameter is not within the nominal range.

30. The method of claim 27 wherein said actively adjusting a resonant frequency includes actively adjusting with the controller at least one of a variable capacitance or a variable inductance of the tank circuit.

31. The method of claim 27 wherein said actively adjusting a resonant frequency includes actively adjusting with the controller a variable impedance element.

32. An inductive power supply for supplying power to a remote device having a secondary inductor in electrical communication with a load, the remote device can be selectively placed in proximity to the inductive power supply to wirelessly receive power from the inductive power supply, the inductive power supply comprising:
    a tank circuit having a primary inductor for wirelessly transferring power to the remote device having said secondary inductor in electrical communication with said load by an inductive coupling, wherein a resonant frequency of said tank circuit is based at least in part on said load;
    an inverter for applying power to said tank circuit, said inverter applying power to said tank circuit at a variable operating frequency and a duty cycle;
    a DC power source coupled to said inverter to supply DC power to said inverter, said DC power source having a rail voltage;
    a drive circuit coupled to said inverter, said drive circuit dictating said variable operating frequency and said duty cycle; and
    a controller for dynamically reconfiguring the inductive power supply, said controller configured to monitor at least one operational characteristic of the inductive power supply, said controller configured to actively vary said variable operating frequency of said inverter such that said variable operating frequency is at or near said resonant frequency, wherein variations in said variable operating frequency affect said at least one operational characteristic, said controller configured to actively vary, based on said at least one operational characteristic, said resonant frequency of said tank circuit.

33. The inductive power supply of claim 32 wherein said controller is configured to monitor said at least one operational characteristic of the inductive power supply to determine if the inductive power supply is operating efficiently, said controller configured to reconfigure the inductive power supply upon a determination that the inductive power supply is not operating efficiently.

34. The inductive power supply of claim 32 wherein said controller is configured to search for the most efficient inductive power supply configuration to deliver power to the remote device by repeatedly reconfiguring the inductive power supply by repeatedly varying one of said resonant frequency of said tank circuit, said operating frequency of said inverter, said duty cycle of said inverter and said rail voltage of said DC power source.

* * * * *